(12) United States Patent
Hosaka

(10) Patent No.: US 10,932,659 B2
(45) Date of Patent: Mar. 2, 2021

(54) LED-TYPE DISTAL END OPTICAL ADAPTER

(71) Applicant: OLYMPUS CORPORATION, Tokyo (JP)

(72) Inventor: Yoichi Hosaka, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 439 days.

(21) Appl. No.: 15/901,939

(22) Filed: Feb. 22, 2018

(65) Prior Publication Data

US 2018/0242831 A1 Aug. 30, 2018

(30) Foreign Application Priority Data

Feb. 24, 2017 (JP) .............................. JP2017-033502

(51) Int. Cl.
| | | |
|---|---|---|
| *A61B 1/06* | (2006.01) | |
| *A61B 1/00* | (2006.01) | |
| *A61B 1/05* | (2006.01) | |
| *G02B 23/24* | (2006.01) | |

(52) U.S. Cl.
CPC ........ *A61B 1/0676* (2013.01); *A61B 1/00096* (2013.01); *A61B 1/0607* (2013.01); *A61B 1/0684* (2013.01); *A61B 1/00101* (2013.01); *A61B 1/00108* (2013.01); *A61B 1/051* (2013.01); *G02B 23/2461* (2013.01); *G02B 23/2476* (2013.01)

(58) Field of Classification Search
CPC . A61B 1/00096; A61B 1/0676; A61B 1/0684; A61B 1/0607; G02B 23/2461; G02B 23/2476; H04N 5/2252; H04N 5/2256
See application file for complete search history.

(56) References Cited

U.S. PATENT DOCUMENTS

| | | | |
|---|---|---|---|
| 6,796,939 B1 * | 9/2004 | Hirata ................ | A61B 1/00036 600/109 |
| 2005/0177027 A1 * | 8/2005 | Hirata .................... | A61B 1/128 600/179 |
| 2006/0058584 A1 * | 3/2006 | Hirata .................. | A61B 1/0623 600/179 |
| 2006/0183977 A1 * | 8/2006 | Ishigami .............. | A61B 1/0684 600/179 |
| 2007/0112247 A1 * | 5/2007 | Hirata .................. | A61B 1/0684 600/101 |
| 2013/0137925 A1 * | 5/2013 | Ushijima ............. | A61B 1/0008 600/109 |

FOREIGN PATENT DOCUMENTS

| | | |
|---|---|---|
| JP | 2004-248835 A | 9/2004 |
| JP | 2011-133662 A | 7/2011 |

* cited by examiner

*Primary Examiner* — Aaron B Fairchild
(74) *Attorney, Agent, or Firm* — Scully, Scott, Murphy & Presser, P.C.

(57) ABSTRACT

An LED-type distal end optical adapter includes a three-dimensional molded substrate including a through hole and provided with a mounting surface and wall surface parts provided so as to project from the mounting surface, an adapter frame member including a small diameter hole in which an outer circumferential surface of the first wall surface part of the three-dimensional molded substrate is disposed and forming a first adhesive filling space, and a lens holding frame disposed in a through hole and forming a second adhesive filling space.

14 Claims, 6 Drawing Sheets

LED-TYPE DISTAL END OPTICAL ADAPTER

CROSS REFERENCE TO RELATED APPLICATION

This application claims the benefit of Japanese Application No. 2017-33502 filed in Japan on Feb. 24, 2017, the contents of which are incorporated herein by this reference.

BACKGROUND OF THE INVENTION

Field of the Invention

The present invention relates to an LED-type distal end optical adapter provided with an LED mounting substrate.

Description of the Related Art

Insides of living bodies, plants and the like are objects to be diagnosed or inspected by endoscopes. For this reason, a light source is necessary to illuminate an observation target. Endoscopes configured to irradiate an observation target with light emitted from a light-emitting element are proposed these days.

For example, Japanese Patent Application Laid-Open Publication No. 2004-248835 discloses an endoscope with LED illumination disposed at a distal end portion of an insertion portion. In contrast, Japanese Patent Application Laid-Open Publication No. 2011-133662 discloses an endoscope apparatus that implements selective switching among a plurality of types of light-emitting element groups in a simple configuration.

A plurality of LED chips described in Japanese Patent Application Laid-Open Publication No. 2004-248835 are disposed in their respective countersunk holes. A radiation direction side of each LED chip is covered with a semi-transparent sealing material. A cover glass is disposed on a front face of the sealing material in close contact with the front face of the sealing material under a predetermined pressure.

A plurality of LED chips described in Japanese Patent Application Laid-Open Publication No. 2011-133662 are provided in an illumination unit constituting a distal end adapter. In FIG. 4 of Japanese Patent Application Laid-Open Publication No. 2011-133662, an LED chip 13B2 is electrically connected to an electrode pattern formed on a mounting surface of an illumination substrate 13C with a bonding wire or the like. A fluorescent substance dispersed resin 13E is provided on the front side of the illumination substrate 13C so as to cover the LED chip 13B2. Furthermore, a protective coating resin 13K is provided on the front side of the fluorescent substance dispersed resin 13E so as to cover the fluorescent substance dispersed resin 13E.

The sealing material and the protective coating resin are preferably made of a material that does not hinder light emission of the LED as much as possible and have high transparency.

BRIEF SUMMARY OF THE INVENTION

An LED-type distal end optical adapter according to an aspect of the present invention includes a light-emitting element configured to emit illumination light, a three-dimensional molded substrate including a through hole and provided with a mounting surface on which the light-emitting element is mounted and a wall surface part provided so as to project from the mounting surface, an adapter frame member including a hole in which the wall surface part of the three-dimensional molded substrate is disposed and forming a first adhesive filling space for filling a gap between the adapter frame member and the wall surface part with an adhesive and a lens holding frame disposed in the through hole and forming a second adhesive filling space for filling a gap between the lens holding frame and the wall surface part.

DETAILED DESCRIPTION OF THE PREFERRED EMBODIMENTS

Figure 1:
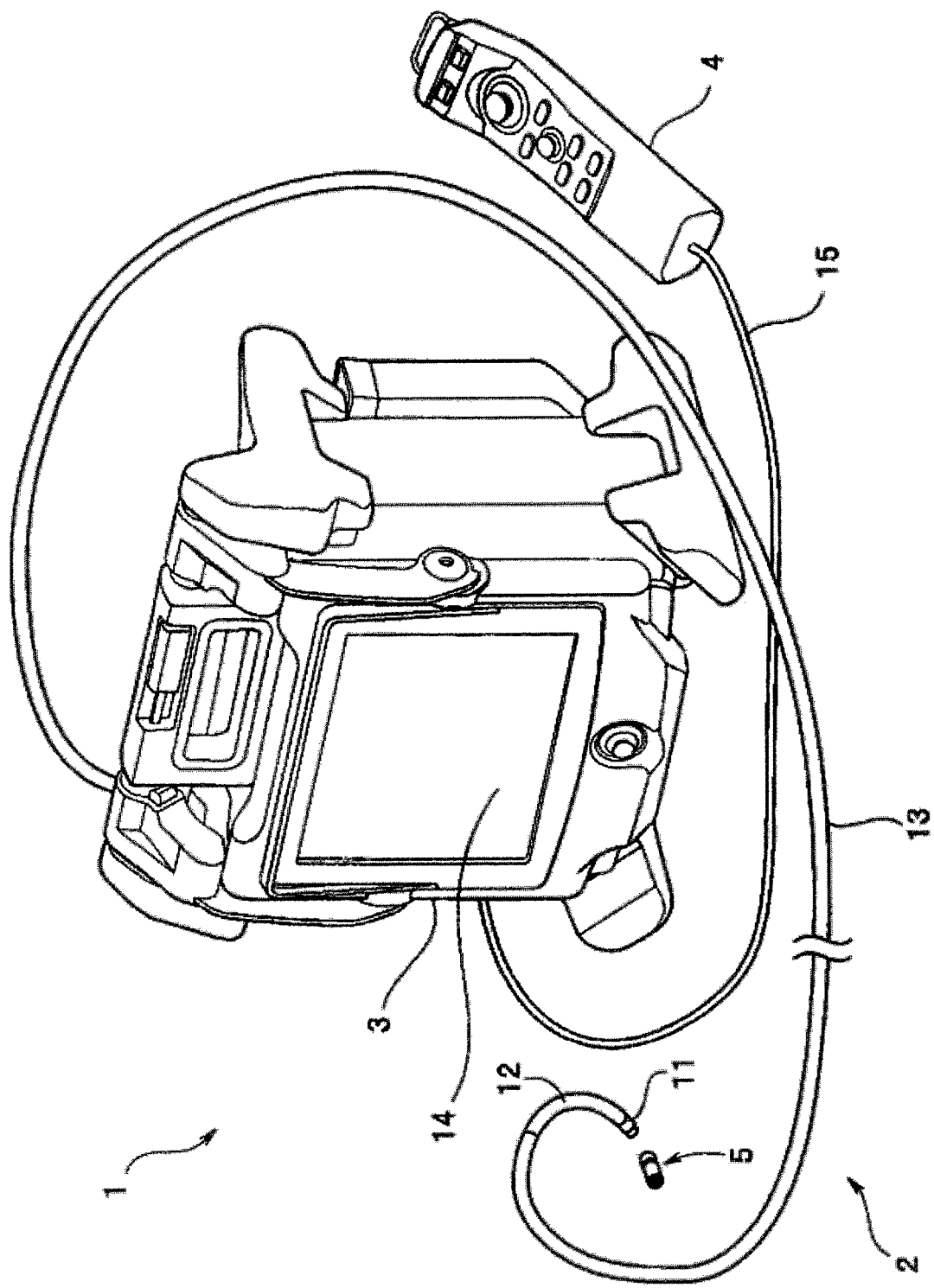
FIG. 1 is a diagram describing an endoscope apparatus to which an LED-type distal end optical adapter can be detachably attached.

Hereinafter, an embodiment of the present invention will be described with reference to the accompanying drawings.

Note that among drawings used in the following description, scales of some drawings are changed for each component so that each component is shown in a recognizable size in each drawing. That is, the present invention is not limited only to the numbers of components, shapes of the components, ratio in size among the components and relative positional relationships among the respective components described in the drawings.

As shown in FIG. 1, an endoscope apparatus 1 is constructed of an elongated insertion portion 2, a body section 3 connected to a proximal end portion of the insertion portion 2 and an operation portion 4 connected to the body section 3. The insertion portion 2 is constructed of a distal end portion 11, a bending portion 12 and a flexible tube portion 13 continuously connected in order from a distal end side. An image pickup device such as a CCD or a C-MOS is provided at the distal end portion 11. Reference numeral 5 denotes an LED-type distal end optical adapter (hereinafter abbreviated as "distal end adapter") which is designed to be detachably attached to the distal end portion 11.

The body section 3 incorporates a central processing unit (CPU), a ROM, a RAM, an image processing section, a light source and a large-capacity storage apparatus. Reference numeral 14 denotes a display apparatus 14 which is attached to the body section 3. The display apparatus 14 is configured to display an endoscope image picked up by the image pickup device at the distal end portion 11.

The operation portion 4 is connected to the body section 3 via a cable 15. The operation portion 4 includes various operation members such as a joystick and a freeze button. For example, a user of the endoscope apparatus 1 can bend the bending portion 12 of the insertion portion 2 in a desired direction by operating the joystick. The user of the endoscope apparatus 1 can cause the display apparatus 14 to display a still image by operating the freeze button.

Figure 2:
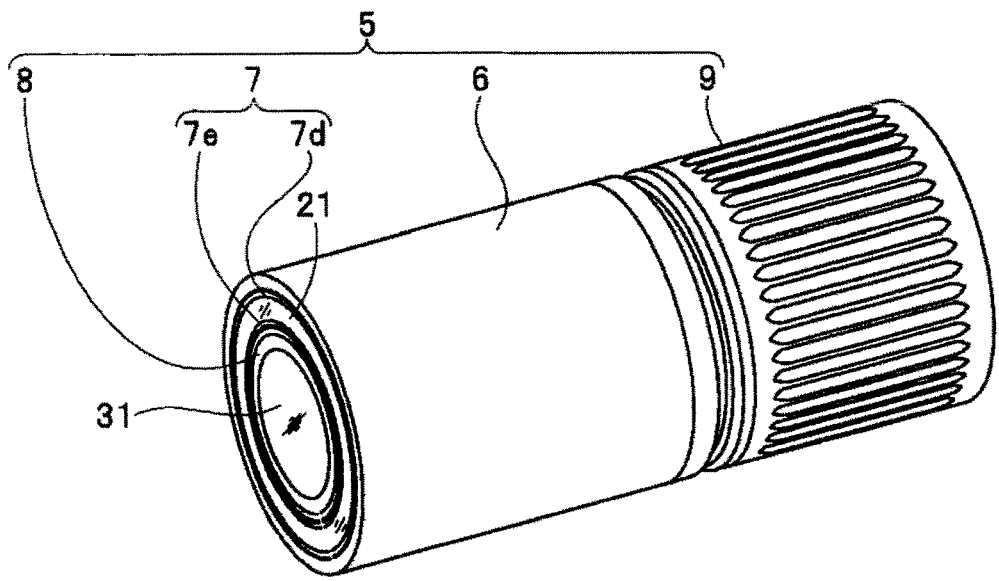
FIG. 2 is a diagram describing the LED-type distal end optical adapter.
Figure 3:
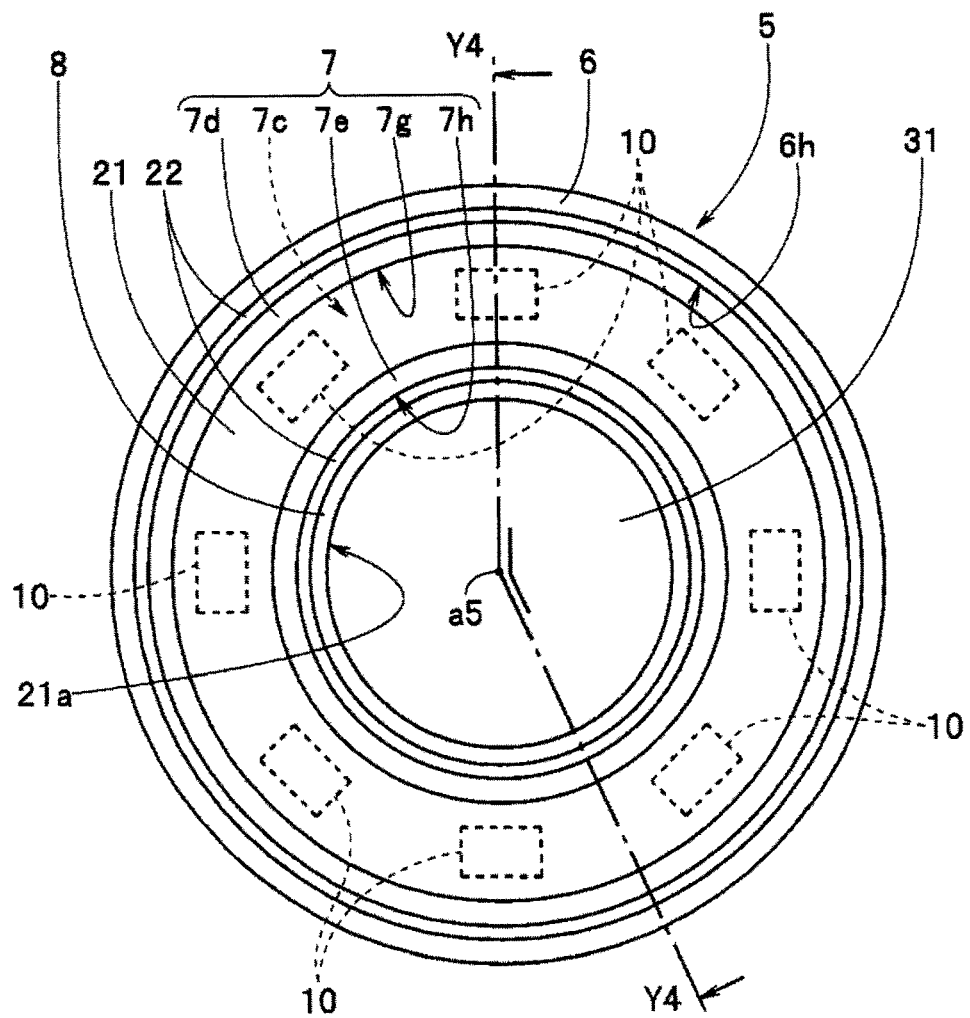
FIG. 3 is a front view of the LED-type distal end optical adapter.

As shown in FIG. 2 and FIG. 3, the distal end adapter 5 mainly includes an adapter frame member 6, a three-dimensional molded substrate 7, a lens holding frame 8, a retaining ring 9 and light-emitting elements 10. The light-emitting element 10 is, for example, an LED chip. The retaining ring 9 has a cylindrical shape and is rotatably externally fitted to a proximal end portion of the adapter frame member 6. A female thread (not shown) is formed on an inner circumferential surface on a proximal end opening side of the retaining ring 9.

Note that reference numeral 7d denotes a first wall surface part, reference numeral 7e denotes a second wall surface part, reference numeral 21 denotes sealing resin and reference numeral 31 denotes a distal end lens. Reference numeral 22 in FIG. 3 denotes an adhesive.

Hereinafter, the adapter frame member 6, the three-dimensional molded substrate 7 and the lens holding frame 8 will be described.

Figure 4:
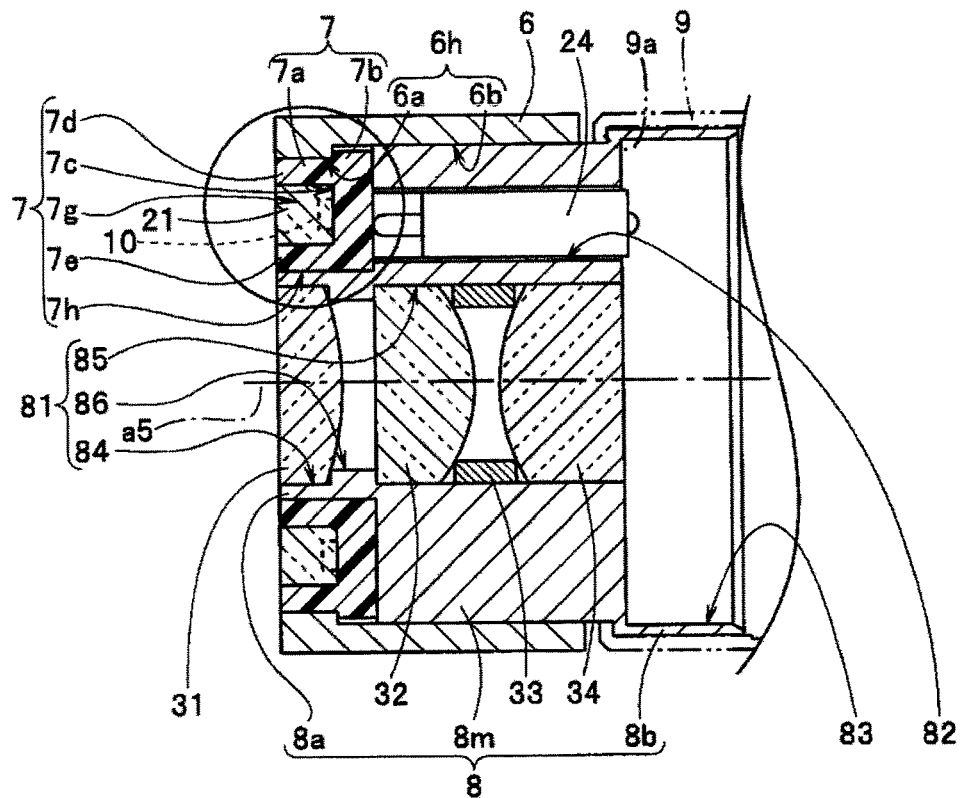
FIG. 4 is a cross-sectional view along a line Y4-Y4 in FIG. 3 and is a diagram describing a configuration of the LED-type distal end optical adapter.
Figure 5:
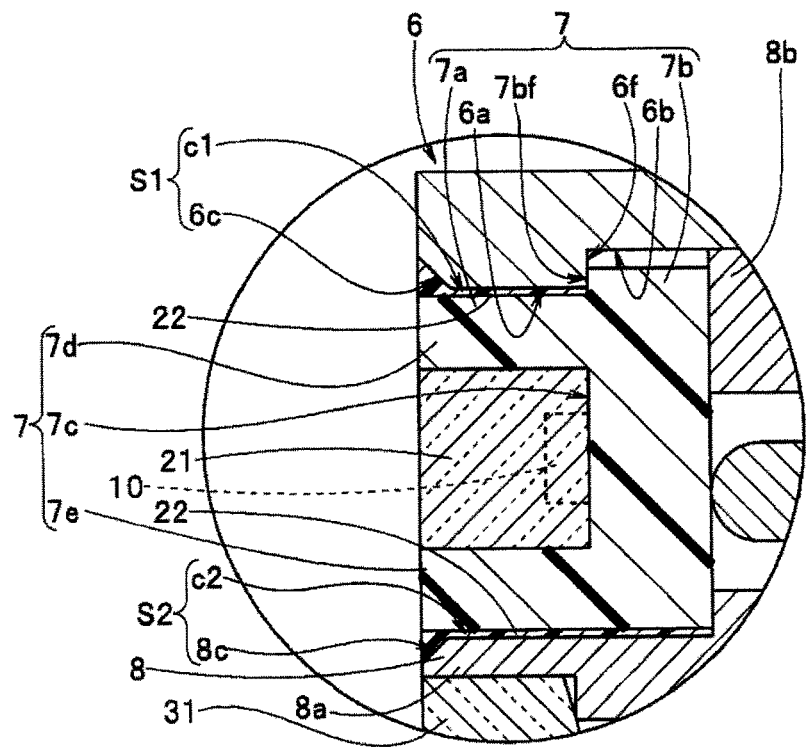
FIG. 5 is an enlarged view of a part shown by an arrow Y5 in FIG. 4.
Figure 6A:
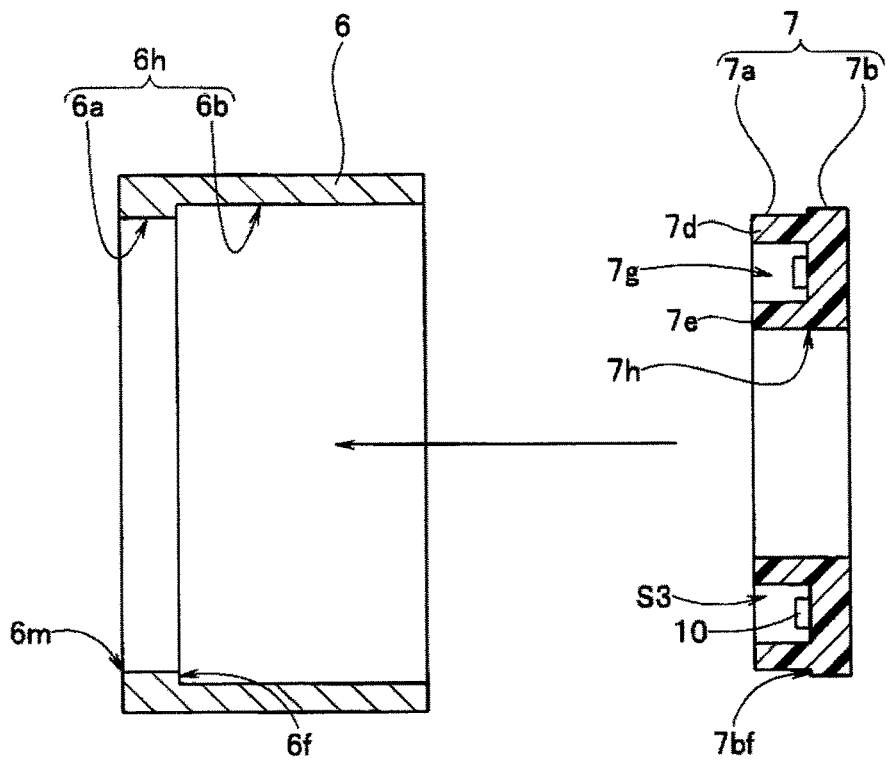
FIG. 6A is a diagram describing an assembly step of the LED-type distal end optical adapter and describing a procedure for disposing a three-dimensional molded substrate in an adapter frame member.

The adapter frame member 6 is a cylindrical exterior member. As shown in FIG. 3, FIG. 4 and FIG. 6A, the adapter frame member 6 includes a stepped hole 6h. The stepped hole 6h includes a small diameter hole 6a which is a first hole including a distal end opening 6m and a large diameter hole 6b which is provided closer to the proximal end side than the small diameter hole 6a and which is a second hole, an inner diameter of which is larger than the small diameter hole 6a. As shown by an arrow in FIG. 6A, the three-dimensional molded substrate 7 is arranged into the stepped hole 6h. Reference numeral 6f in FIG. 5 and FIG. 6C denotes a stepped surface. The stepped surface 6f functions as a holding surface.

The three-dimensional molded substrate 7 is made of, for example, low-temperature co-fired ceramics (LTCC). The three-dimensional molded substrate 7 is formed into a predetermined shape by laminating a plurality of layers and a plurality of contact portions (not shown) and a plurality of inner layer wirings (not shown) are provided at predetermined positions.

As shown in FIG. 4 and FIG. 6A, the three-dimensional molded substrate 7 includes a through hole 7h and has an annular shape. The through hole 7h is a center through hole formed at a center of the three-dimensional molded substrate 7. The three-dimensional molded substrate 7 includes a small diameter portion 7a and a flange portion 7b. The flange portion 7b is a large-diameter portion projecting outward from an outer circumferential surface of the small diameter portion 7a. Reference numeral 7bf denotes a distal end face of the flange portion 7b and has a function of abutting the stepped surface 6f.

The three-dimensional molded substrate 7 is provided with a mounting surface 7c, a first wall surface part 7d provided so as to project from the mounting surface 7c and a second wall surface part 7e. The outer circumferential surface of the first wall surface part 7d is an outer circumferential surface of the small diameter portion 7a. On the other hand, the inner circumferential surface of the second wall surface part 7e is an inner circumferential surface of the through hole 7h and is a distal end side portion.

Figure 6B:
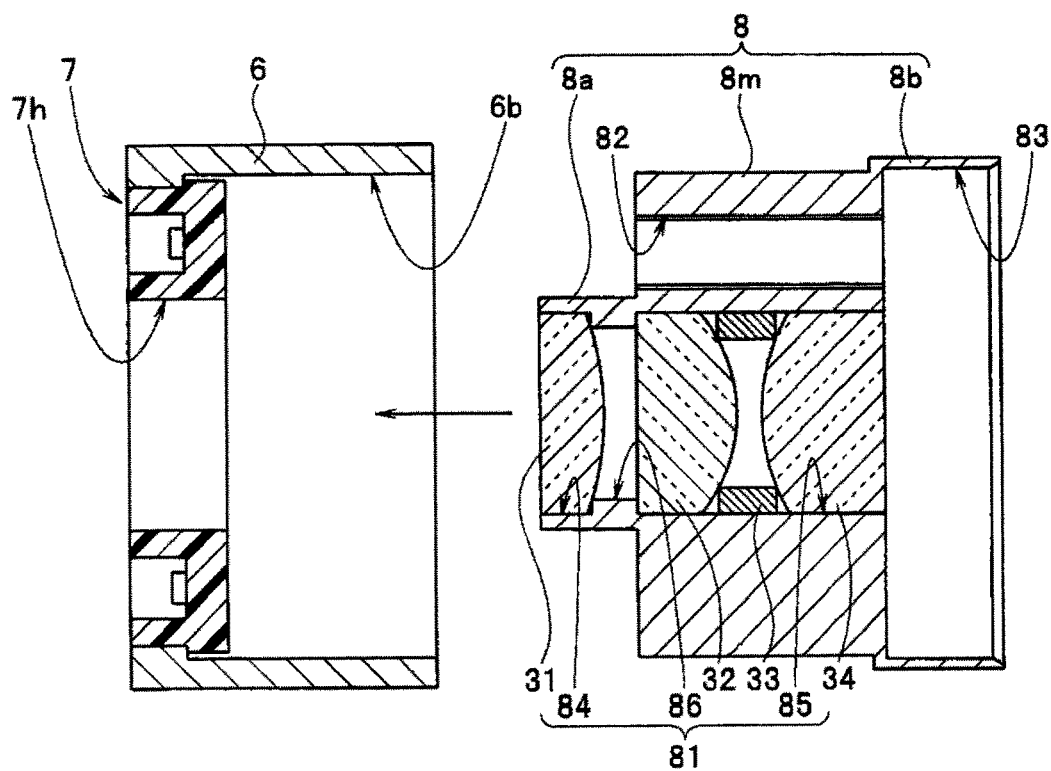
FIG. 6B is a diagram describing an assembly step of the LED-type distal end optical adapter and is a diagram describing a procedure for disposing a lens holding frame in the adapter frame member in which the three-dimensional molded substrate is disposed.
Figure 6C:
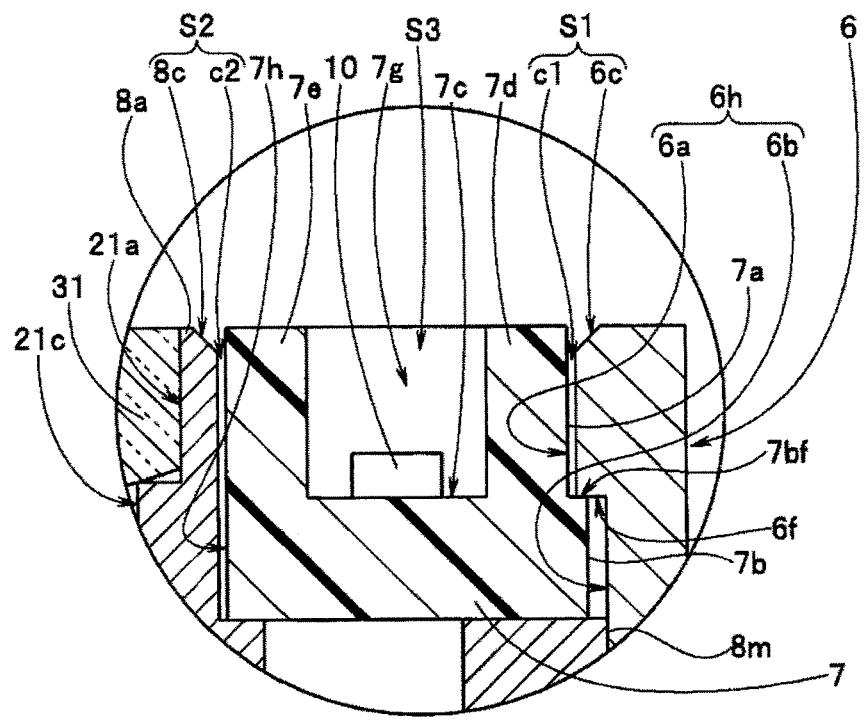
FIG. 6C is a diagram describing a first adhesive filling space which is filled with an adhesive and a second adhesive end point space.

As shown in FIG. 6C, the distal end face 7bf of the flange portion 7b of the three-dimensional molded substrate 7 abuts the stepped surface 6f, the small diameter portion 7a is thereby disposed in the small diameter hole 6a and the flange portion 7b is disposed in the large diameter hole 6b.

With the distal end face 7bf being disposed in contact with the stepped surface 6f, the distal end face of the first wall surface part 7d becomes substantially flush with the distal end face of the adapter frame member 6. Note that with the distal end face 7bf being disposed in contact with the stepped surface 6f, the distal end face of the adapter frame member 6 may be made to project from the distal end face of the first wall surface part 7d. Making the distal end face of the adapter frame member 6 project from the distal end face of the first wall surface part 7d makes it possible to protect the lens surface or the substrate in an event of collision with a subject or the like.

The small diameter hole 6a is a hole in which the first wall surface part 7d is disposed and a first gap c1 between the inner circumferential surface of the small diameter hole 6a and the first wall surface part 7d constitutes a first adhesive filling space S1 to be filled with an adhesive 22. In the present embodiment, the first adhesive filling space S1 includes the first gap c1 and a first notch portion 6c which is a cut surface.

The first notch portion 6c is a cut surface, a so-called surface C provided along a ridgeline of the distal end opening 6m of the adapter frame member 6 in FIG. 6A and FIG. 6C. The ridgeline of the distal end opening 6m of the adapter frame member 6 refers to a part where the distal end face of the adapter frame member 6 and the inner circumferential surface of the small diameter hole 6a cross each other. The three-dimensional molded substrate 7 is fixed to the adapter frame member 6 by the adhesive 22 that fills the first adhesive filling space S1.

The mounting surface 7c is a bottom surface of a circumferential groove 7g. The depth of the circumferential groove 7g is set to a predetermined depth from the distal end face of the wall surface parts 7d and 7e. A plurality of contact portions (not shown) are provided in order on the mounting surface 7c, for example, at equal intervals in the circumferential direction. Light-emitting elements 10 are electrically connected to the plurality of contact portions as respectively shown in FIG. 3.

In the present embodiment, the three-dimensional molded substrate 7 is provided with the circumferential first wall surface part 7d provided on the substrate outer circumferential surface side through the circumferential groove 7g and the through hole 7h and the circumferential second wall surface part 7e provided on the inner circumferential surface side of the through hole 7h. In other words, in the present embodiment, the mounting surface 7c is positioned between the inner circumferential surface of the first wall surface part 7d and the outer circumferential surface of the second wall surface part 7e opposite to the inner circumferential surface. The concave portion constructed of the inner circumferential surface of the first wall surface part 7d, the mounting surface 7c and the outer circumferential surface of the second wall surface part 7e is a sealing member filling space S3 which is filled with the transparent or semi-transparent sealing resin 21.

Note that in the present embodiment, the inner circumferential surface of the first wall surface part 7d and the outer circumferential surface of the second wall surface part 7e have a function as a reflection surface that reflects light emitted from the light-emitting elements 10 and passing through the sealing resin 21.

As shown in FIG. 4 and FIG. 6B, the lens holding frame 8 of the present embodiment has a cylindrical shape and includes one objective optical hole 81 provided at the center, for example, a pair of connection member holes 82 and a distal end portion arrangement space 83. A predetermined region (not shown) of the distal end portion 11 constituting the insertion portion 2 is housed in the distal end portion arrangement space 83 in a predetermined state. Electrical connection pins (reference numeral 24 in FIG. 4) are disposed in the connection member holes 82.

The objective optical hole 81 includes, for example, a distal end lens hole 84, an optical lens arrangement hole 85 and a communication hole 86. The communication hole 86 is a hole configured to communicate an inside of the distal end lens hole 84 with an inside of the optical lens arrangement hole 85. A distal end lens 31 is fixed to the inside of the distal end lens hole 84. A plurality of optical members such as a first optical lens 32, an interval ring 33 and a second optical lens 34 are fixed in the optical lens arrangement hole 85. The optical members are not limited to the two optical lenses 32 and 34, and the interval ring 33, but may be one or three or more optical lenses, a plurality of interval rings, one or a plurality of apertures or the like.

The lens holding frame 8 includes a distal end small diameter portion 8a, a proximal end large diameter portion 8b and an intermediate portion 8m disposed between the distal end small diameter portion 8a and the proximal end large diameter portion 8b. The distal end small diameter portion 8a of the lens holding frame 8 is disposed in the through hole 7h of the three-dimensional molded substrate 7. A second gap c2 between an inner circumferential surface of the second wall surface part 7e which is an inner circumferential surface of the through hole 7h and an outer circumferential surface of the distal end small diameter portion 8a constitutes a second adhesive filling space S2 to be filled with the adhesive 22. In the present embodiment, the second adhesive filling space S2 is constructed of the second gap c2 and a second notch portion 8c which is a cut surface.

The second notch portion 8c is a cut surface, a so-called surface C, provided along an outer circumferential side ridgeline of the distal end face of the distal end small diameter portion 8a of the lens holding frame 8. The outer circumferential side ridgeline of the distal end face of the distal end small diameter portion 8a of the lens holding frame 8 refers to a portion where the distal end face of the distal end small diameter portion 8a and the outer circumferential surface cross each other. The lens holding frame 8 is fixed to the three-dimensional molded substrate 7 by the adhesive 22 with which the second adhesive filling space S2 is filled.

Note that the intermediate portion 8m of the lens holding frame 8 is formed so as to be disposed in the large diameter hole 6b of the stepped hole 6h of the adapter frame member 6. While the distal end face of the intermediate portion 8m disposed in the large diameter hole 6b is in contact with the proximal end face of the three-dimensional molded substrate 7, the distal end face of the distal end small diameter portion 8a becomes substantially flush with the distal end face of the second wall surface part 7e of the three-dimensional molded substrate 7. In the present embodiment, while the distal end face of the intermediate portion 8m is in contact with the proximal end face of the three-dimensional molded substrate 7, the distal end face of the adapter frame member 6 projects from the distal end face of the distal end small diameter portion 8a in order to protect the lens surface in the event of collision with the subject or the like.

Note that an inner circumferential surface of a slip-off preventing part (reference numeral 9a in FIG. 4) of the retaining ring 9 is slidably disposed on the outer circumferential surface of the intermediate portion 8m. The inner circumferential surface of the retaining ring 9 is slidably disposed on the outer circumferential surface of the proximal end large diameter portion 8b. The slip-off preventing part 9a is a circumferential convex portion projecting in a central axis a5 direction.

Here, an assembly procedure of the distal end adapter 5 will be described with reference to FIG. 6A to FIG. 6C.

When assembling the distal end adapter 5, the operator prepares the adapter frame member 6, the three-dimensional molded substrate 7, the lens holding frame 8 and the retaining ring 9.

Note that the light-emitting elements 10 are mounted on the mounting surface 7c of the three-dimensional molded substrate 7 in advance. The lens holding frame 8 is provided with optical members such as the lenses 31, 32 and 34, and the interval ring 33. Furthermore, the retaining ring 9 is slidably disposed with respect to the intermediate portion 8m and the proximal end large diameter portion 8b of the lens holding frame 8 in advance. In FIG. 6B, the retaining ring 9 is not shown.

First, the operator disposes the three-dimensional molded substrate 7 in the stepped hole 6h of the adapter frame member 6 as shown in FIG. 6A. Then the operator disposes the distal end face 7bf of the flange portion 7b on and in contact with the stepped surface 6f of the stepped hole 6h. As a result, the outer circumferential surface of the first wall surface part 7d is disposed in the small diameter hole 6a of the stepped hole 6h.

Next, after inserting the retaining ring 9, the operator inserts the lens holding frame 8 into the large diameter hole 6b of the stepped hole 6h of the adapter frame member 6 in which the three-dimensional molded substrate 7 is arranged as shown in FIG. 6B. The operator then inserts the distal end small diameter portion 8a into the through hole 7h of the three-dimensional molded substrate 7 arranged in the stepped hole 6h of the adapter frame member 6, and then inserts the distal end small diameter portion 8a further into the back. As a result, the distal end face of the intermediate portion 8m comes into contact with the proximal end face of the three-dimensional molded substrate 7 and the distal end face of the distal end small diameter portion 8a is disposed to be substantially flush with the distal end face of the second wall surface part 7e. After inserting the adapter frame member 6 into the lens holding frame 8, the operator fixes the adapter frame member 6 and the lens holding frame 8 from the side face using a screw (not shown). Note that after inserting the lens holding frame 8 into the three-dimensional molded substrate 7, the lens holding frame 8 together with the three-dimensional molded substrate 7 may be inserted into the adapter frame member 6.

As a result, as shown in FIG. 6C, the first adhesive filling space S1 constructed of the first notch portion 6c and the first gap c1 provided between the distal end face of the first wall surface part 7d and the distal end face of the adapter frame member 6, the second adhesive filling space S2 constructed of a second notch portion 8c and the second gap c2 provided between the distal end face of the second wall surface part 7e and the distal end face of the distal end small diameter portion 8a which is the distal end face of the lens holding frame 8, and the sealing member filling space S3 are provided separately from each other. That is, the wall surface parts 7d and 7e function as boundary parts that divide the first adhesive filling space S1, the second adhesive filling space S2 and the sealing member filling space S3.

Here, the operator fills the first adhesive filling space S1 and the second adhesive filling space S2 with the adhesive 22. As a result, the three-dimensional molded substrate 7 is bonded and fixed to the adapter frame member 6 and the lens holding frame 8 is bonded and fixed to the three-dimensional molded substrate 7 which is bonded and fixed to the adapter frame member 6. Furthermore, the operator seals the light-emitting elements 10 by filling the inside of the circumferential groove 7g which is the sealing member filling space S3 with the sealing resin 21. As a result, the distal end adapter 5 shown in FIG. 3 to FIG. 5 is assembled.

The substrate mounted with the light-emitting elements 10 is used as the three-dimensional molded substrate 7 provided with an inner layer wiring, the flange portion 7b having a surface abutting the three-dimensional molded substrate 7 is provided, and on the other hand, the stepped hole 6h provided with the stepped surface 6f is provided to prevent the three-dimensional molded substrate 7 from slipping off by the abutting surface contacting the adapter frame member 6 in which the three-dimensional molded substrate 7 is housed and disposed. In addition, the circumferential groove 7g, a bottom surface of which becomes the mounting surface 7c is formed on the three-dimensional molded substrate 7 to provide the sealing member filling space S3 constructed of the first wall surface part 7d, the mounting surface 7c and the second wall surface part 7e. Furthermore, the first notch portion 6c which can become the first adhesive filling space S1 is formed on the distal end face of the adapter frame member 6 adjacent to the distal end face of the first wall surface part 7d and the second notch portion 8c which can become the second adhesive filling space S2 is formed on the distal end face of the distal end small diameter portion 8a adjacent to the distal end face of the second wall surface part 7e. Note that the first notch portion 6c and the second notch portion 8c may have a rectangular shape instead of the cut surface.

As a result, it is possible to easily assemble the three-dimensional molded substrate 7 and the lens holding frame 8 into the adapter frame member 6, and since the first adhesive filling space S1, the second adhesive filling space S2 and the sealing member filling space S3 are clearly divided by the wall surface parts 7d and 7e, it is possible to improve workability in easily and reliably filling the first adhesive filling space S1 and the second adhesive filling space S2 with the adhesive 22 and improve workability in filling the sealing member filling space S3 with the sealing resin.

Therefore, it is possible to reliably and quickly fill the inside of the first adhesive filling space S1 and the inside of the second adhesive filling space S2 with the adhesive 22 and firmly and stably fix the three-dimensional molded substrate 7 and the lens holding frame 8 to the adapter frame member 6. Furthermore, adhesion of the adhesive 22 to the sealing resin 21 can reliably prevent the illumination optical path from being blocked. This extends a range of choices of the adhesive 22.

Note that in the aforementioned embodiment, the first adhesive filling space S1 is formed of the first gap c1 and the first notch portion 6c and the second adhesive filling space S2 is formed of the second gap c2 and the second notch portion 8c.

Figure 6D:
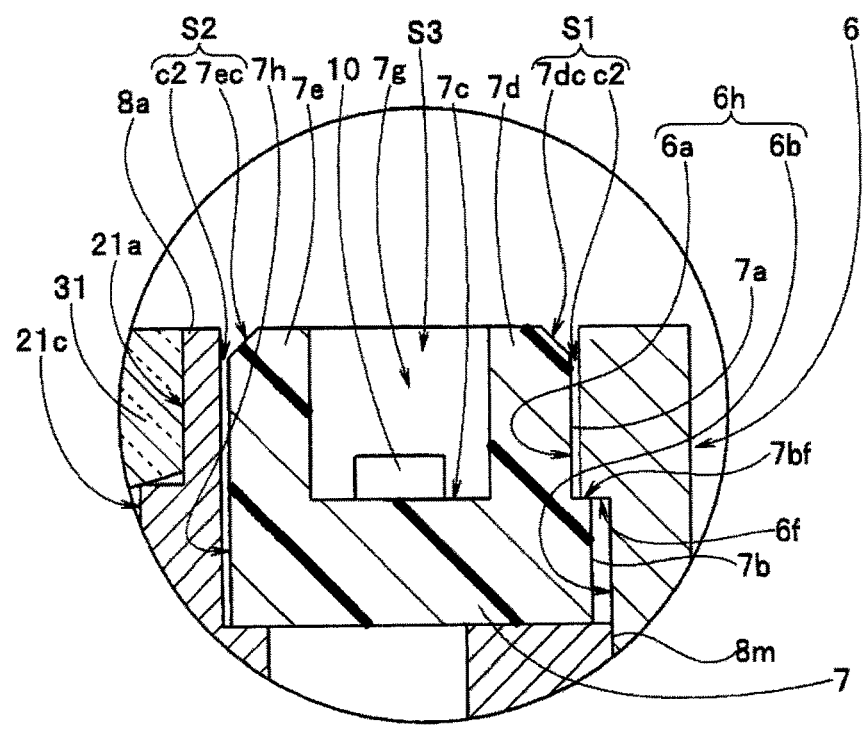
FIG. 6D is a diagram describing another configuration example of the first adhesive filling space which is filled with an adhesive and another configuration example of the second adhesive end point space.

However, as shown in FIG. 6D, it is also possible to form the first adhesive filling space S1 of the first gap c1 and a first notch portion 7dc provided in a first wall surface 7d and form the second adhesive filling space S2 of the second gap c2 and a second notch portion 7ec provided in a second wall surface 7e. The first notch portion 7dc is provided along an outer circumferential side ridgeline of the distal end face of the first wall surface part 7d and the second notch portion 7ec is provided along a ridgeline of the distal end opening of the through hole of the second wall surface part 7e. The outer circumferential side ridgeline of the distal end face of the first wall surface part 7d refers to a part where the distal end face of the first wall surface part 7d and the outer circumferential surface of the small diameter portion 7a cross each other. The ridgeline of the distal end opening of the through hole of the second wall surface part 7e refers to a part where the distal end face and the inner circumferential surface of the second wall surface part 7e cross each other. The inner circumferential surface of the second wall surface part 7e refers to the inner circumferential surface of the through hole 7h.

Figure 6E:
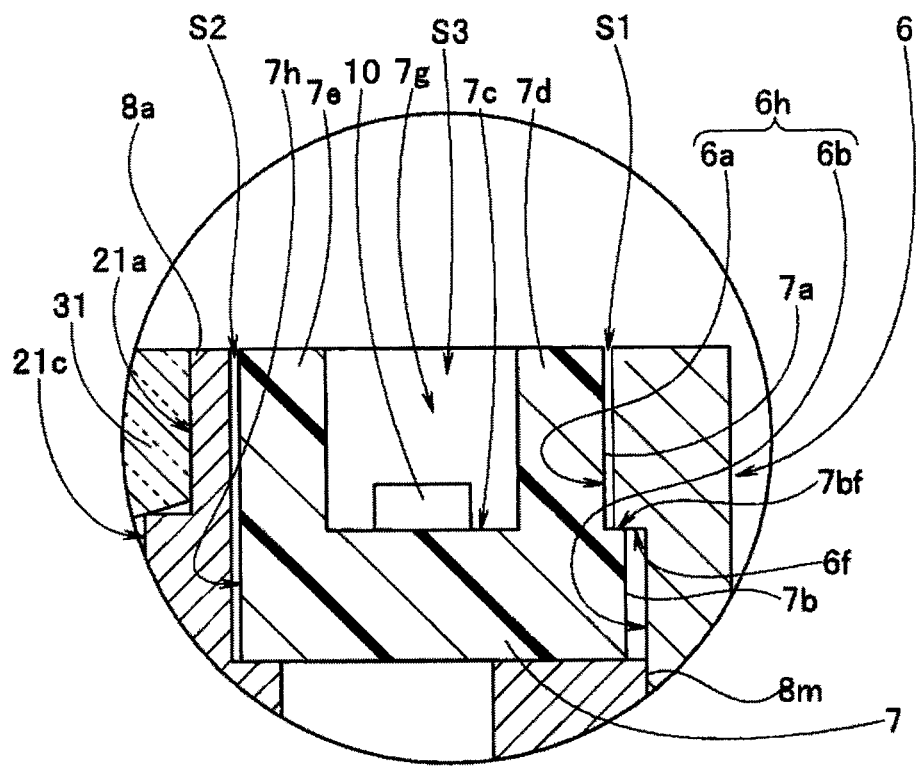
FIG. 6E is a diagram describing another configuration example of the first adhesive filling space which is filled with an adhesive and another configuration example of the second adhesive end point space.

Furthermore, as shown in FIG. 6E, the first adhesive filling space S1 may be formed of the first gap c1 without providing the aforementioned first notch portions 6c and 7dc and the second adhesive filling space S2 may be formed of the second gap c2 without providing the aforementioned second notch portions 8c and 7ec.

Note that as the adhesive, one having a certain degree of flexibility even after hardening may be used suitably. When the adhesive is used, a clearance of the first gap c1 between the small diameter hole 6a of the adapter frame member 6 and the small diameter portion 7a of the three-dimensional molded substrate 7 and a clearance of the second gap c2 between the through hole 7h of the three-dimensional molded substrate 7 and the distal end small diameter portion 8a are set to a predetermined relatively large gap and the adhesive is poured into the gap. In this way, stronger and more stable bonding and fixing may be implemented after hardening.

Note that the present invention is not limited only to the aforementioned embodiment but can be implemented modified in various ways without departing from the spirit and scope of the present invention.

What is claimed is:

1. A distal end optical adapter comprising:
   an electrically powered light source configured to emit illumination light;
   a three-dimensional molded substrate including a through hole, the three-dimensional molded substrate being provided with an annular mounting surface on which the light source is mounted, the three-dimensional molded substrate further having first and second walls provided so as to each project from the mounting surface;
   an adapter frame including a hole in which the three-dimensional molded substrate is disposed such that a first adhesive filling space is formed between the adapter frame and one of the first and second walls, the first adhesive filling space being filled with an adhesive; and
   a lens holding frame disposed in the through hole such that a second adhesive filling space is formed between the lens holding frame and an other of the first and second walls, the second adhesive filling space being filled with the adhesive.

2. The distal end optical adapter according to claim 1, wherein the first wall comprises a circumferential first wall provided on an outer circumferential side of the three-dimensional molded substrate and the second wall comprises a circumferential second wall provided on a through hole side of the three-dimensional molded substrate.

3. The distal end optical adapter according to claim 2, wherein a concave portion comprising an inner circumferential surface of the circumferential first wall, the mounting surface and an outer circumferential surface of the circumferential second wall define a sealing member filling space, the sealing member filling space being filled with a sealing resin.

4. The distal end optical adapter according to claim 3, wherein the first adhesive filling space, the second adhesive filling space and the sealing member filling space are divided by the circumferential first wall and the circumferential second wall.

5. The distal end optical adapter according to claim 2, wherein
the first adhesive filling space comprises a first gap between an inner circumferential surface of the hole of the adapter frame and an outer circumferential surface of the circumferential first wall, and
the second adhesive filling space comprises a second gap between an outer circumferential surface of the lens holding frame and an inner circumferential surface of the circumferential second wall.

6. The distal end optical adapter according to claim 5, wherein the first adhesive filling space further comprises a first notch provided along a ridgeline of a distal end opening of the hole of the adapter frame or an outer circumferential side ridgeline of a distal end face of the circumferential first wall.

7. The distal end optical adapter according to claim 5, wherein the second adhesive filling space further comprises a second notch portion provided along an outer circumferential side ridgeline of a distal end face of the lens holding frame or a ridgeline of a distal end opening of the through hole of the circumferential second wall.

8. The distal end optical adapter according to claim 1, wherein the three-dimensional molded substrate comprises a small diameter portion and a large diameter portion projecting outward from an outer circumferential surface of the small diameter portion, a distal end face of the large diameter portion functioning as an abutting surface, and
the adapter frame comprises a first hole in which the small diameter portion of the three-dimensional molded substrate is disposed and a second hole in which the large diameter portion of the three-dimensional molded substrate is disposed.

9. The distal end optical adapter of claim 1, wherein the light source is an LED.

10. A distal end optical adapter comprising:
an electrically powered light source configured to emit illumination light;
a three-dimensional molded substrate including a through hole, the three-dimensional molded substrate being provided with an annular mounting surface on which the light source is mounted, the three-dimensional molded substrate further having first and second walls provided so as to each project from the mounting surface;
an adapter frame including a hole in which the three-dimensional molded substrate is disposed; and
a lens holding frame disposed in the through hole;
wherein one or more of:
a first adhesive filling space is formed between the adapter frame and the first wall with the first adhesive filling space being filled with an adhesive; or
a second adhesive filling space is formed between the lens holding frame and the second wall with the second adhesive filling space being filled with the adhesive.

11. The distal end optical adapter according to claim 10, wherein:
the first wall comprises an outer circumferential wall provided on an outer circumferential side of the three-dimensional molded substrate; and
the first adhesive filling space is formed between the adapter frame and the outer circumferential wall.

12. The distal end optical adapter according to claim 10, wherein:
the second wall comprises an inner circumferential wall provided on a through hole side of the three-dimensional molded substrate; and
the second adhesive filling space is formed between the lens holding frame and the inner circumferential wall.

13. The distal end optical adapter according to claim 10, wherein:
the first wall comprises an outer circumferential wall provided on an outer circumferential side of the three-dimensional molded substrate and the second wall comprises an inner circumferential wall provided on a through hole side of the three-dimensional molded substrate;
the first adhesive filling space is formed between the adapter frame and the outer circumferential wall; and
the second adhesive filling space is formed between the lens holding frame and the inner circumferential wall.

14. The distal end optical adapter of claim 10, wherein the light source is an LED.

* * * * *